Figure 1:
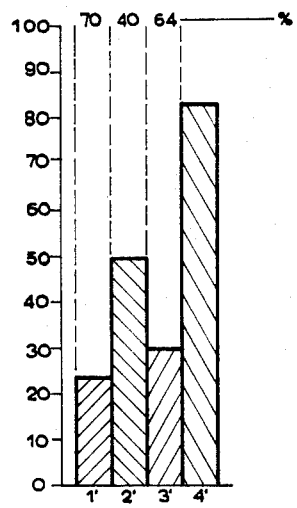

United States Patent [19]

Scalesciani

[11] Patent Number: 4,499,104
[45] Date of Patent: Feb. 12, 1985

[54] IMIDAZOLE COMPOUND, THE PROCESS FOR ITS PREPARATION, AND THERAPEUTICALLY ACTIVE COMPOSITIONS CONTAINING SAME

[75] Inventor: Juan Scalesciani, Buenos Aires, Argentina

[73] Assignee: Farmatis S.r.l., Milan, Italy

[21] Appl. No.: 796,532

[22] Filed: May 31, 1977

[30] Foreign Application Priority Data

May 13, 1976 [FR] France .................. 76 14381

[51] Int. Cl.$^3$ ............................ A61K 31/415
[52] U.S. Cl. .................. 514/396; 548/346
[58] Field of Search ............ 548/346; 424/273 R

[56] References Cited

U.S. PATENT DOCUMENTS 3,657,441  4/1972  Jensen et al. .......... 424/273 R
4,152,441  5/1979  Van der Stelt ............ 548/342

FOREIGN PATENT DOCUMENTS 91242  12/1972  German Democratic Rep. .................. 548/546

OTHER PUBLICATIONS

Ellis et al., J. Pharm. Pharmacol. 1964, vol. 16, pp. 400–407.
Katritzky et al., Advances in Heterocyclic Chemistry, vol. 12, p. 114 New York, Academic Press, 1970.
Novelli et al., Tetrahedron Letters 1967, No. 3, pp. 265–269.
Davidson et al., J. Org. Chem. 1938, vol. 2, pp. 319–327.
Lombardino et al., J. Med. Chem. 1974, vol. 17, pp. 1182–1188.
Weidenhagen et al., Berichte 1937, vol. 70B, pp. 570–583.
Weidenhagen et al., Chem. Abst. 1937, vol. 31, cols. 3914–3915.
Morgenstern et al., Chem. Abst. 1975, vol. 83, No. 157696t.
Chemical Abstracts, vol. 83 Chemical Substance Index, I–Ph Jul.–Dec. 1975, p. 2688CS.
Wilkinson et al., Chem. Abst. 1975, vol. 82, No. 39231u.
Chemical Abstracts, vol. 82 Chemical Substance Index, Dib–Peo Jan.–Jun. 1975, p. 2186CS.
Yartseva et al., Chem. Abst. 1972, vol. 76, No. 86541f.
Chemical Abstracts, vol. 76 Chemical Substance Index, E–O Jan.–Jun. 1972, p. 1774CS.

*Primary Examiner*—Richard A. Schwartz
*Attorney, Agent, or Firm*—Stevens, Davis, Miller & Mosher

[57] ABSTRACT

A new compound 4-(p.chlorophenyl)-5-methylimidazole is provided. A method of preparing the new compound from p-chlorobenzoyl-methylcarbinol by reacting the formamide or ammonium formate at high temperature is described. The compound is useful as an antiinflammatory, analgesic and antipyretic agent.

3 Claims, 4 Drawing Figures

IMIDAZOLE COMPOUND, THE PROCESS FOR ITS PREPARATION, AND THERAPEUTICALLY ACTIVE COMPOSITIONS CONTAINING SAME

This invention relates to a new imidazole compound, the preferred process for its preparation, and therapeutic compositions containing same as the active ingredient.

More precisely, the present invention relates to the compound 4-(p-chlorophenyl)-5-methylimidazole of the formula:

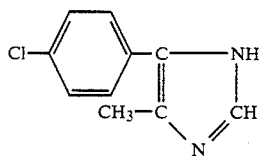

and its acid addition salts.

Imidazole compounds of this general type have been previously prepared (Tetrahedron Letters No. 3, pp. 265–269, 1967), but as yet the compound of formula (I) has not been known and the therapeutic properties have not been recognized for this type compound.

It has now been found that the compound of formula (I) possesses strong antiinflammatory, analgesic and antipyretic activity and may be used in human therapy. The effectiveness of this compound is considerably greater than many of the best non-steriod antiinflammatory-analgesic compounds commercially available at present.

The new compound may therefore be used in all fields of human therapy in which antiinflammatory, analgesic and antipyretic agents are applied, and will produce results which are unexpectedly superior to those obtainable by the use of known products for the same therapeutic uses.

The novel 4-(p-chlorophenyl)-5-methylimidazole of this invention can be economically prepared on a commercial scale by reacting p-chlorobenzoyl-methylcarbinol with ammonium formate or, optionally, with formamide.

The reaction is preferably conducted without solvents, by heating the reaction mixture for several hours at a temperature between about 170° C. and about 190° C. The formamide or ammonium formate are always used in large excess over the amount of carbinol.

On termination of the reaction, the reaction mixture is poured into water and the pure product is separated from the aqueous solution. For greater clarity, the preparation of the 4-(p-chlorophenyl)-5-methylimidazole is illustrated in the following example for preparation in one of its preferred embodiments, but which is non-limiting.

The p-chlorobenzoyl-methylcarbinol is a known starting material readily available in accordance with known methods of manufacture.

It should be understood that the hydrogen atom in the imidazole ring may be in a state of tautomeric equilibrium and all such forms are encompassed by this disclosure. Also within the scope of the present invention are the non-toxic pharmaceutically acceptable salts of 4-(p-chlorophenyl)-5-methylimidazole including acid addition salts, quaternary salts and alkaline earth metal salts such as the sodium potassium and calcium salts. Typical of said acid addition salts are, for example, those formed by treatment with mineral acids as, for example, the hydrochloride, hydrobromide or hydroiodide and the like. The said salts are prepared by methods known to the art. For example, the sodium or potassium salt may be prepared by addition of an equivalent amount of sodium or potassium hydroxide to a solution of the substituted imidazole compound. The salt is then obtained by concentrating the reaction mixture and evaporating to dryness.

The 4(p-chlorophenyl)-5-methylimidazole of this invention or its pharmaceutically acceptable salts can be administered alone or in association with a pharmaceutically acceptable carrier in the form of tablets, elixirs, capsules and the like. These preparations may be made by any of the known pharmaceutical methods. For example, in tablet form, they are compounded with inert ingredients which may include a suitable binder material such as, for example, gums, starches and sugars. They may be incorporated into gelatin capsules or elixirs which have the advantage of being susceptible to flavoring by the addition of available natural or synthetic flavoring materials. Similarly colorants can be added to the compounded forms. The compound may be generally adminstered in compositions so proportioned as to afford a unit dosage of 20 to 100 mg. Larger or smaller doses can be provided or single units can be made to facilitate fractional use such as scored tablets. Ordinarily the preferred dosage level will be between about 100 and about 500 mg. daily depending upon the individual needs of the patient and the recommendation of the attending physician. The dosage may be increased or decreased as necessary depending upon the severity of the condition or it may be varied during the course of treatment.

The following examples and pharmacology are given for purposes of illustrating the preparation of the novel pharmaceutically active 4-(p-chlorophenyl)-5-methylimidazole of this invention and its pharmacological effects but it is not to be considered as limiting the invention in any way. This data is considered to be significant in illustrating the surprising activity of the new compound. For simplicity the compound is referred to hereinafter as chlorophenazole.

Specific Embodiments

EXAMPLE 1.

Preparation of Chlorophenazole

Ammonium formate (120 g) and p-chlorobenzoyl-methylcarbinol (50 g) are heated for 6 hours at 180° C.

After this time the reaction is complete, and the reaction mixture is poured into water.

The aqueous solution is acidified with hydrochloric acid, purified with activated carbon and hot filtered to afford the hydrochloride salt of chlorophenazole.

The 4-(p-chlorophenyl)-5-methylimidazole, also referred to as chlorophenazole, is precipitated by treating the said hydrochloride with an ammonium or alkaline base such as sodium hydroxide. The resulting produce is purified by recrystallization from ethanol to afford chlorophenazole.

The pure base has a M.P. of 198° C., while the hydrochloride salt has a M.P. of 217° C.

EXAMPLE 2

Pharmacological activity of chlorophenazole

The activity of the new compound has been studied and determined by a large number of pharmacological tests. For reference these tests have in all cases been carried out in comparison with known drugs having similar pharmacological activity.

The pharmacological tests may be grouped as follows:

(1) Antiedematous activity
(2) Analgesic activity
(3) Antipyretic activity
(4) Neuropharmacological activity
(5) Action on the cardiovascular and respiratory system.

(1) Study of the antiedematous activity.

(a) Edema by carrageen

A 1% physiological solution of carrageen was used. Rats of the Wistar-Roux-Ocefa stock having a weight of 150±30 g were used. The drugs were suspended in 1% carboxymethylcellulose or dissolved in distilled water and administered orally one hour before the inflammatory agent in a volume of 0.5 ml/100 g. The carrageen was adminstered subcutaneously in the subplanetary region of one of the rear paws. The volume of the paw was measured platysmagraphically initially and then after 1.5 hour, 3 hours and 5 hours after administering the carrageen. One inflammation unit was defined as the displacement of 0.01 ml of Hg.

The edema was evaluated as the difference in volume of the rear paw before and after the carrageen. The DE 50 was calculated by the probits method and graphically. The comparison drugs used were phenylbutazone and niflumic acid.

The chlorophenazole proved to be more active than phenylbutazone, only slightly more active than niflumic acid but much less toxic than the latter. The activity manifested by the chlorophenazole at the 3rd-5th hour was of particular interest, and is believed to be related to the inhibition of the prostaglandins (Tables 1-2).

TABLE 1

| Products | Dose mg/kg | Number of rats | Time in hours 1.5 | 3 | 5 |
|---|---|---|---|---|---|
| Controls | | 22 | 33 | 62 | 75 |
| Chlorophenazole | 10 | 18 | 15 | 35 | 58 |
| Chlorophenazole | 20 | 18 | 15 | 29 | 44 |
| Chlorophenazole | 40 | 18 | 15 | 23 | 42 |
| Controls | | 12 | 30 | 81 | 100 |
| Phenylbutazone | 10 | 12 | 28 | 65 | 88 |
| Phenylbutazone | 20 | 12 | 26 | 59 | 74 |
| Phehylbutazone | 40 | 12 | 24 | 51 | 73 |
| Controls | | 12 | 37 | 88 | 100 |
| Niflumic acid | 10 | 12 | 25 | 51 | 80 |
| Niflumic acid | 20 | 12 | 20 | 35 | 56 |
| Niflumic acid | 40 | 12 | 18 | 33 | 49 |

Δ Volume = volume of the inflamed paw at time $T_x$ (1.5, 3, 5) - volume of the same paw before inflammation at time $T_o$.
The figures represent the Δ volumes for the inflamed paw in platysmographical inflammation units (UPI). 1 UPI = 0.01 ml Hg.

TABLE 2

| Products | DE$_{50}$ mg/Kg os | DL$_{50}$ mg/Kg os | IT DL$_{50}$/DE$_{50}$ |
|---|---|---|---|
| Chlorophenazole | 7 | 515 | 73.60 |
| Phenylbutazone | 15 | 351 | 23.40 |
| Niflumic acid | 7 | 30 | 11.40 |

(b) Edema by carrageen in adrenoprival rats

To evaluate if the activity of the chlorophenazole on edema by carrageen was influenced by stimulation of the suprarenes, experiments were carried out with suprarenectomised rats. Normal rats were also compared with falsely operated rats to evaluate the influence of the operational trauma. It can be concluded that the activity of the chlorophenazole is independent of the suprarenal cortex (Table 3).

TABLE 3

| Products | Dose mg/kg | Number of rats | Time in hours 1.5 | 3 | 5 |
|---|---|---|---|---|---|
| Normal control rats | | 7 | 26 | 73 | 75 |
| Normal rats with chlorophenazole | 10 | 18 | 15 | 35 | 58 |
| | 20 | 18 | 15 | 29 | 44 |
| | 40 | 18 | 15 | 23 | 42 |
| Falsely operated rats | | 7 | 23 | 73 | 74 |
| Adrenoprival rats | | 7 | 25 | 45 | 66 |
| Adrenoprival rats with chlorophenazole | 10 | 10 | 22 | 27 | 55 |
| | 20 | 10 | 16 | 18 | 45 |
| | 40 | 10 | 13 | 20 | 39 |
| Adrenprival rats with niflumic acid | 10 | 7 | 25 | 34 | — |
| | 20 | 7 | 20 | 24 | — |
| | 40 | 7 | 19 | 30 | — |

(c) Pulminary edema by carrageen

Using the Sancilio method (Sancilio F. L., J. Pharmacol. Exptl. Therap., 168, 199 (1969); Sancilio L. F. Rodrigues R., Proc. Soc. Exptl. Biol. Med., 123, 707 (1969); Sancilio L. F. Lawrence R., Proc. Soc. Exptl. Biol. Med., 127, 597 (1968), pulminary irritation was induced in Wistar-Roux-Ocefa rats and the capacity of chlorophenazole and other drugs to prevent production of pleural exudate was measured. 5 ml of a 0.025% carrageen solution and 0.075% Evans blue were injected into the pleurea.

The action of chlorophenazole, mepyrazole and phenylbutazone were evaluated from the quantity of exudate present in the pleural cavity after 1 and 6 hours.

The chlorophenazole and phenylbutazone are significantly active (Table 4).

TABLE 4

| Products | Dose mg/Kg | Number of rats | ml of exudate |
|---|---|---|---|
| Controls | 0 | 20 | 4.65 |
| Chlorophenazole | 30 | 20 | 3.11 |
| Phenylbutazone | 30 | 20 | 3.12 |
| Mepyrazole | 30 | 20 | 4.38 |

(2) Study of analgesic activity.

(a) Stretching by acetic acid (chemical stimulus)

Twelve mice of both sexes, Rockland-Roux-Ocefa stock of weight 23-25 g were used per group. The drugs were administered orally 30 minutes before i.p. injection of 0.1 ml/10 g of 0.6% acetic acid. The animals were observed for 20 minutes noting the number of stretches. Chlorophenazole showed a very good analgesic activity, decidedly better than that of the clonixine (Table 5) and mepyrazole (FIG. 1).

In FIG. 1 curve I refers to controls, curve II to phenylbutazone (35 mg/kg) while curve III refers to chlorophenazole. The curves give the variation of the temperature on the time over the temperature of basis.

TABLE 5

| Products | Dose mg/kg | Number of rats | Numer of stretches/ 20 min. | % effect |
|---|---|---|---|---|
| Controls | | 48 | 85 | 0 |
| Chlorophenazole | 21.3 | 24 | 70 | 18 |

TABLE 5-continued

| Products | Dose mg/kg | Number of rats | Numer of stretches/ 20 min. | % effect |
|---|---|---|---|---|
| | 33.0 | 24 | 49 | 42 |
| | 51.0 | 24 | 29 | 66 |
| Clonixine | 27.2 | 24 | 90 | 0 |
| | 42.0 | 24 | 52 | 39 |
| | 64.9 | 24 | 40 | 53 |

(b) Hot plate method (thermal stimulus)

This is based on the time (seconds) taken by the mouse for removing his paws from a plate heated to 56° C. Male mice were used of weight 25 to 27 g, preselected so that all reacted in a time less than 20 seconds.

The reaction time was measured 15, 30 and 60 minutes after administering the drugs. The chlorophenazole was tested orally and subcutaneously, both alone and associated with morphine hydrochloride. Oral administration of 50 mg/kg of chlorophenazole significantly prolongs the reaction time relative to the control mice. It may therefore be stated that the analgesic produced by the chlorophenazole is not only of peripheral origin (as demonstrated by the test on stretching by acetic acid) but implies the participation of a central mechanism (this is also confirmed by the evident increase exerted by the drug on morphine analgesia). (FIGS. 2 and 3).

Figure 2:
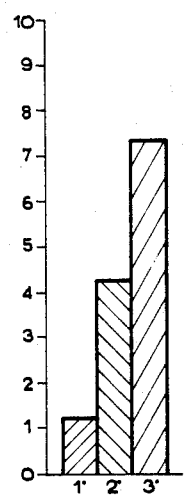
Figure 3:
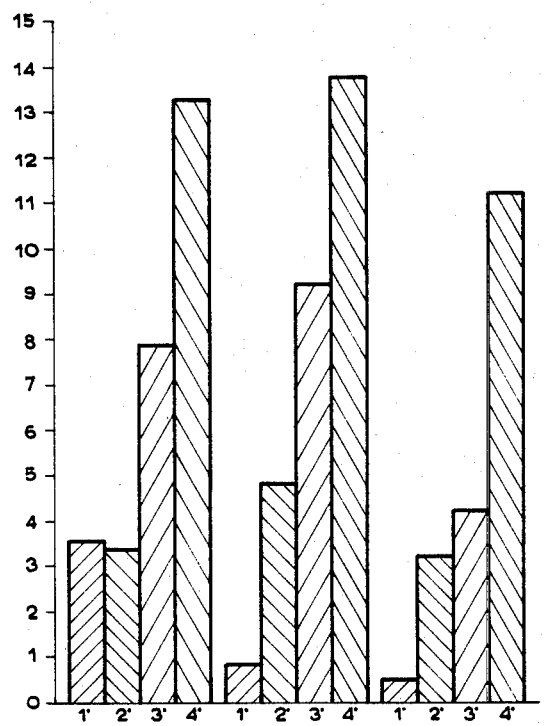

In FIG. 2 curve I refers to chlorophenazole (50 mg/kg), curve 2 to morphine (5 mg/kg), curve 3 to chlorophenazole plus morphine (50 mg/kg chlorophenazole +5 mg/kg morphine). In FIG. 3 the curves I refer to chlorophenazole (50 mg/kg), curves 2 to morphine (5 mg/kg), curves 3 to morphine+chlorophenazole (5 mg/kg+w25 mg/kg respectively), curves 4 refer to morphine+Chlorophenazole (5 mg/kg+50 mg/kg respectively). The first set of curves refers to observations made after 15 minutes from administration of the drugs, and second set refers to observations made after 30 min. and the third set to observations made after 60 min.

(3) Study of antipyretic activity

This was first studied in the rabbit, using 6 male albino rabbits of 3-3.5 kg per group, made hyperthermal by i.v. injection of 0.5 ml/kg of a lysate of Neisseria perflava. The rectal temperature was determined by thermocouples every 60 minutes for 3 hours. The difference in temperature was calculated between maximum elevation and base temperature at each time. The drug was administered orally. The chlorophenazole clearly protected the animals from temperature increase.

It was then measured in the rat using 10 animals of Wistar stock per group weighing 170-200 g, made hyperthermal by subcutaneous injection of a 10% beer yeast suspension in distilled water.

Figure 4:
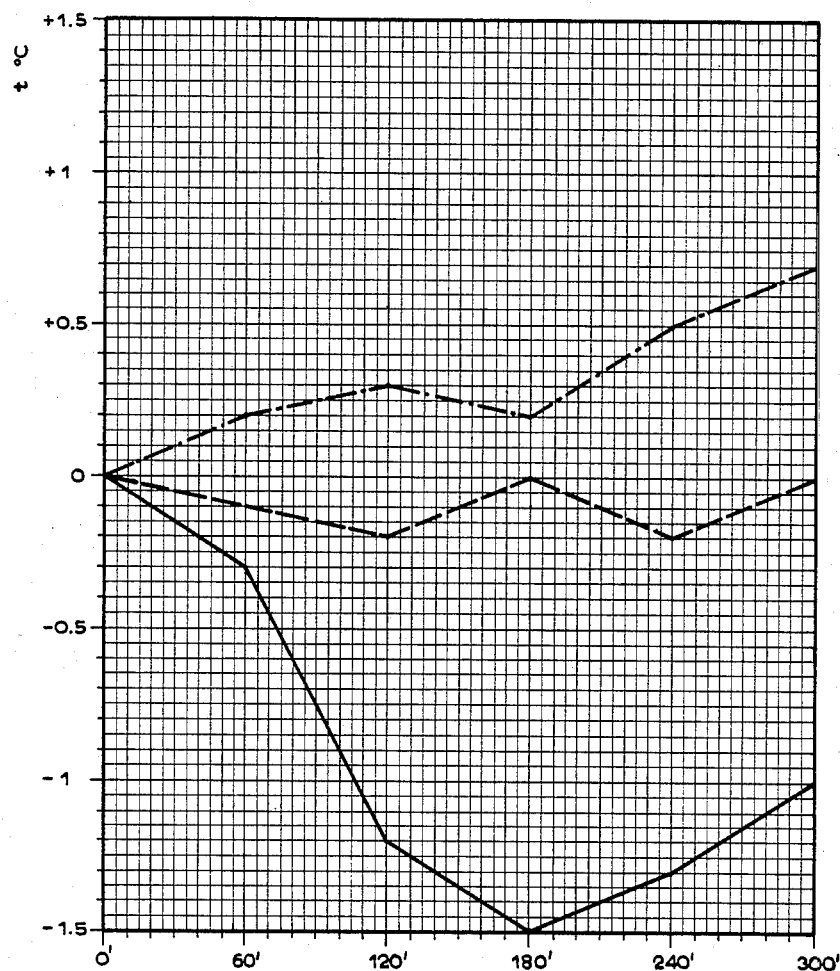

The compounds awere administered orally 60 minutes after the induction of fever in doses equal to 1/10 of the $DL_{50}$. Readings were taken at 30 minute intervals for 5 hours. The activity of the chlorophenazole as an antipyretic and its superiority over phenylbutazone are evident from FIG. 4, in which curve I refers to witnesses, curve II to chlorophenazole (50 mg/kg), curve III to phenylbetazone (35 mg/kg).

(4) Neuropharmacological studies.

(a) Action on sleep by barbiturates.

Phenobarbital sodium was administered i.p. with a dose of 40 mg/kg in Wistar-Ocefa rats of 80-90 g. Loss of the redressment reflex was taken to indicate commencement of sleep. The chlorophenazone was administered orally with a dose of 1/10 of the $DL_{50}$. The induction time and the duration of sleep were measured. The chlrophenazole improves sleep by barbiturates (Table 6).

TABLE 6

| Product | Dose mg/kg | Induction time in minutes | Sleeping time in minutes |
|---|---|---|---|
| Pentobarbital sodium | 40 | 4.4 | 49.1 |
| Chlorophenazole Pentobarbital sodium | 51.5 20 | 2.9 | 65.2 |

(b) Anticonvulsive activity.

Rockland-Ocefa mice of both sexes weighing 22±3 g and fasting for 16 hours were used. The convulsive agents were administered i.p. in doses of 2 mg/kg of strychnine sulphate and 110 mg/kg of cardiazole.

This does not modify the framework of convulsive death but leads to significant elongation of the premortal period (Table 7).

TABLE 7

| Dose in mg/kg of chlorophenazole | Protection from conculsivant | | | | | |
|---|---|---|---|---|---|---|
| | CARDIAZOLE | | | STRYCHNINE | | |
| | 15' | 30' | 90' | 15' | 30' | 90' |
| 0 | 7.90 8.90 | 7.90 5.30 | 7.90 5.30 | 7.1 4.8 | 7.1 4.8 | 7.1 4.8 |
| 50 | 6.23 6.70 | 10.80 8.30 | 8.10 7.0 | 7.0 7.4 | 12.8 12.6 | 8.7 13.8 |
| 100 | 9.90 8.90 | 13.00 26.40 | 28.70 20.00 | 11.7 19.5 | 11.3 13.8 | 9.5 11.5 |
| 200 | — 9.2 | — 27.30 | — 30.10 | 28.6 18.3 | 12.8 16.0 | 18.2 21.0 |

(5) Action on the cardiovascular and respiratory systems.

Male dogs weighing 10-14 kg were used, anaesthetised with pentobarbital sodium in doses of 30 mg/kg administered i.v. The following were recorded: the arterial pressure (with an Hg manometer), respiration with a Marey drum), carotid occlusion, and the response to noradrenaline, acetycholine, histamine, atropine and pyribenzamine.

Rapid i.v. administration of chlorophenazole with a dose of 10 mg/kg induces sudden transient hypotension (not more than 2 min.) of 42 mm Hg, which is not annulled by atropine or by antihistamines. The response to noradrenaline, acetylcholine and the carotid reflex are not modified by the drug. Accompanying the hypotension, there is the classical reflex response of increase in pulmonary ventilation. The transient hypotension effect has a possible peripheral mechanism in vasodilation.

TOXICOLOGY (1) Acute toxicity.
(a) Rat and mouse

| | $DL_{50}$ and L.F. (mg/kg) | |
|---|---|---|
| | Rat | Mouse |
| i.p. | 135 (116-157) | 175 (166-185) |

-continued
TOXICOLOGY (1) Acute toxicity.
(a) Rat and mouse

| $DL_{50}$ and L.F. (mg/kg) | |
|---|---|
| Rat | Mouse |
| os 515 (415–639) | 534 (524–545) |

Death was preceded by a reduction in spontaneous motility, sedation, hypotherma, paralysis.

(b) Rabbit: by intravenous injection $DL_{100}=55$ mg/kg

The final framework is characterised by marked muscular hypotonia, an almost catatonic state and death by respiratory paralysis.

(c) Dog: similar symptomatology. $DL_{100}=50$ mg/kg (2) Chronic toxicity.

Wistar-Ocefa rats of both sexes weighing 70–90 g were used, divided into groups of 30 animals (15 males and 15 females) to a total of 345 animals.

Chlorophenazole and phenylbutazone (reference drug) were administered orally for a period of 60 days in doses of 30–60 mg/kg of chlorophenazole and 8–160 mg/kg of phenylbutazone (first experiment) and for a period of 5 months in doses of 6–12 mg/kg of chlorophenazole and 16 mg/kg of phenylbutazone (second experiment).

The following parameters were determined periodically: behavior, general state, food consumption, body weight, red blood cell number, white blood cell number, leucocite formula, hemoglobin, hematocrit, globular value, total proteins, glycemia, azotemia, cholesterol, total lipids, triglycerides, creatinine, GOT, GPT, urine analysis. At the end of the experiment the animals were sacrificed, their general state was observed, the following organs were weighed: liver, spleen, kidneys, supranenes, ovary and testicles, lungs, heart, stomach.

Results of first experiment:

There is no difference between the control animals and the treated animals with regard to growth curves. Phenylbutazone doses of 80 and 160 mg/kg are significant for azotemia in male rats relative to the control animals. Phenylbutazone doses of 160 mg/kg are highly significant for total lipids relative to the control animals, and the same for cholesterol at the larger doses of chlorophenazole and phenylbutazone.

The drop in proteins with 160 mg/kg of phenylbutazone is significant. The picture is little different in the females. In the case of males, the weight of the liver increased in all the groups treated. The weight of the kidneys also increased significantly for doses of 160 mg/kg of phenylbutazone.

With regard to stomach appearance, this was contract and pale with phenylbutazone, and distended and rose colored with chlorophenazole. In no case were there macroscopic ulcers.

In no case were there any variations in the hematic framework.

Results of the second experiment:

After 5 months of treatment, the male rats show significant alteration in glycemia, with 16 mg/kg of phenylbutazone, and in cholesterol with 6 kg/mg of chlorophenazole. This latter data was not confirmed with the greater dose.

All other parameters were within standard limits. For female rats, significant triglyceride values were obtained with 16 mg/kg of phenylbutazone and a small increase in glycemia with 12 mg/kg of chlorophenazole.

There was no significant variations in hematological values or weight of the organs.

From the aforegoing data, it is evident that chlorophenazole is a strong antiinflamatory analgesic agent, decidedly better than phenylbutazone, niflumic acid, clonixine or mepyrazole.

In addition, the acute toxicity values and, even more so, the therapeutic index are well in excess of those for phenylbutazone.

The pharmacological results have been fully confirmed in human therapy. The new product may be administered orally or may be injected.

Orally, it is preferably administered in the form of tablets containing the free base or one of its salts with a therapeutically acceptable acid, mixed with the usual pharmaceutical inert diluents and auxiliaries.

It should be understood that although this invention has been described with reference to particular embodiments changes and modifications may be made within the intended scope of the following claims.

What is claimed is:

1. A method of effecting antiinflamatory, analgesic and antipyretic activity which comprises administering to the host an effective amount of an active ingredient selected from 4-(p-chlorophenyl)-5-methylimidazole or a non-toxic pharmaceutically acceptable salt thereof and a pharmaceutically acceptable carrier.

2. The method of claim 1 wherein the active ingredient is 4-(p-chlorophenyl)-5-methylimidazole.

3. The method of claim 1 wherein the active ingredient is 4-(p-chlorophenyl)-5-methylimidazole hydrochloride.

* * * * *